United States Patent Office

Re. 25,022
Reissued Aug. 8, 1961

25,022

SPRAYABLE WATER FREE ALCOHOLIC POLY-VINYL-PYRROLIDONE HAIR PREPARATION

Maurice L. Spiegel, Minneapolis, Minn., assignor to La Maur, Inc., Minneapolis, Minn., a corporation of Minnesota No Drawing. Original No. 2,871,161, dated Jan. 27, 1959, Ser. No. 301,989, July 31, 1952. Application for reissue Feb. 9, 1959, Ser. No. 792,240
11 Claims. (Cl. 167—87.1)

Matter enclosed in heavy brackets [ ] appears in the original patent but forms no part of this reissue specification; matter printed in italics indicates the additions made by reissue.

This invention relates to a hair styling composition and more particularly to a composition for appliction to the surface of hair which will give it luster and retain it in the desired set, and to a method of preparation thereof.

Prior to my discovery, many preparations have been proposed for setting the hair and for causing the hair to have a desired degree of luster or brilliance. One class of preparations which have been extensively used are those containing gums such as tragacanth or karaya, which are suspended in a colloidal water solution and applied to the hair with combing and brushing. The hair is then formed in the desired style and upon drying retains the set. The composition, however, must then be brushed and combed from the hair since it has a dry and dull appearance and cracks and breaks when disturbed.

Another class of hair styling preparations includes the lacquers, principally shellac solutions, which are combed or applied to the surface of the hair which has been preformed to the required style and which lacquer will dry to a hard surface film which gives the hair a sculptural appearance. The hair has a high degree of luster but again cannot be disturbed without cracking and breaking the film. Furthermore, the lacquers may be insoluble in water and require considerable combing and brushing together with washing or other chemical treatment to remove entirely the lacquer film preparatory to a new application. The use of all these previous setting compositions thus entail considerable effort in the application and removal thereof and much time is consumed in their use, especially in time required for drying the gum preparations which are placed in water suspension.

In the course of experimentation with the view of finding a hair styling preparation which lacked either the sticky characteristics of the natural gums, or the cracking and breaking characteristics of shellac, I discovered that the compound known as polyvinylpyrrolidone would furnish a beautiful luster to hair, and also the desired styling qualities without the detrimental characteristics found in the prior art substances. Polyvinylpyrrolidone is a polymerization product of the N-vinyl pyrrolidone monomer having the following formula:

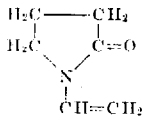

For purposes of application to the hair to produce a high luster, quick drying film, the polymerized N-vinyl pyrrolidone may be combined in an alcoholic solution with a propellant of the class known as Freon, so as to be applied as a spray.

An object of the invention is to provide a hair setting composition embodying a polymerization product of N-vinyl pyrrolidone that may be easily and quickly applied to the hair by combining said material in a solution with mutually compatible substances that will permit application to the hair by spraying.

Another object is to be able to provide controlled flexibility of the film by combining a plasticizer with the other materials forming the composition.

In order to apply the film of polymerized N-vinyl pyrrolidone to the surface of the hair and achieve the desired results in a short time, I may dissolve the product in a quick drying solvent, such as ethyl alcohol. Since polymerized N-vinyl pyrrolidone is soluble in both alcohol and water, it is not critical if there is a negligible quantity of water present in the alcohol. However, where my hair styling composition is to be used in a syray-type container having self-generated pressure, I have found that it is possible to use an alcoholic solution of the polymerized N-vinyl pyrrolidone with dichlorodifluoromethane (or related compounds and mixtures thereof [commonly known in the trade as] *sold under the trademark* Freon) as the propellant.

It is known that dichlorodifluoromethane is a nontoxic and useful propellant for many spray compounds, such as insect sprays, deodorants, etc. However, dichlorodifluoromethane is insoluble in water and, therefore, will not be miscible in any appreciable extent with compounds containing water as a component. I have found that by dissolving the polymerized N-vinyl pyrrolidone compound in absolute alcohol, I can form a solution which is soluble in dichlorodifluoromethane.

In order to make the preparation according to a representative formula, I dissolve from 4 to 8 ounces of powdered solid polyvinylpyrrolidone with sufficient 200 proof (absolute) ethyl alcohol to make one gallon of solution and then chill the resultant solution below room temperature. Then, I add 105 ounces of dichlorodifluoromethane which has been chilled below its boiling temperature (−29° C. to −35° C.) and immediately place the mixture in its bottled container before it can vaporize or take on moisture from the air.

It is undestood, of course, that there is considerable latitude in the proportions of solvent which I may employ, and that there is, likewise, latitude in the percentage of solid polyvinylpyrrolidone which is placed in solution. I do not desire, however, to exceed 8% of solids in the alcohol fraction where dichlorodifluoromethane is employed. A greater percentage of solids is apt to cause gumming of the orifice in the spray container, and may offer difficulty in applying an even film, where the operator does not exercise care. On the other hand, I do not prefer to have an alcohol solution which is more dilute than 4% of solids, since the solvent will be unnecessarily excessive and merely wasted in achieving the desired film upon the hair. Since quick drying is one of the advantages which I obtain it is, therefore, not desirable to require too great an amount of solvent in order to leave the proper thickness of film upon the hair.

I achieve a still further advantage with my unusual hair styling composition by not only furnishing a film with a useful flexibility, but may even further control the plasticity or flexibility of the film to suit individual tastes by the addition of a plasticizer. Thus, by adding a small amount of di-ethyl phthalate, normally in the order of ⅜ of 1 percent, I can materially increase the flexibility or plasticity of the applied film. It is, of course, not desirable to make the film so pliable as not to function properly in setting the hair. The amount of di-ethyl phthalate above mentioned will give a very good quality of flexibility to the hair under average conditions. Where a stiffer film is desired as will more nearly approach the lacquer type of appearance, the di-ethyl phthalate may be omitted. Where the opposite result is desired the diethyl phthalate content may be accordingly increased.

An important property of my composition is its ability to become softened with a slight amount of water which, upon drying, will again leave the film in its lustrus condition and with the desired setting property. Thus, where a lady has styled her hair and through mishap the coiffure becomes disarranged, it is possible for her to brush or comb in a slight amount of water for dampening without requiring a long drying period, and after rearranging, the hair will immediately resume it set and luster. The foregoing has been accomplished without the necessity of completely removing the composition, and then reapplying after a careful and tedious preconditioning of the hair.

Since the polyvinylpyrrolidone cannot be applied to the hair in any other fashion than from a solution, preferably of a quick drying nature, it is an important adjunct to my composition that the proper method be employed in the preparation of the material which will be immediately applicable to the hair to form the film having the unusual characteristics above noted and without further attention thereto. Such method consists in dissolving polyvinylpyrrolidone in a quick drying solution having a non-toxic nature.

Of the solvents tried, I prefer alcohols and particularly ethyl alcohol. Where my method of preparation is for the purpose of obtaining a self-propelling composition, I mix mutually the polyvinylpyrrolidone with absolute alcohol and dichlorodifluoromethane. It is advantageous, because of the low boiling point of the dichlorodifluoromethane, to first mix the polyvinylpyrrolidone with absolute alcohol, then add the propellant subsequently.

It may thus be seen that I have provided a hair styling composition having unusual properties in lusterizing and setting the hair which may be quickly and easily applied and yet which may be quickly and easily removed, the composition being both water soluble and alcohol soluble, and additionally soluble in the self generating propellant, dichlorodifluoromethane, when mutually dissolved in the anhydrous alcohol. It is also to be noted that my invention comprises two extremely simple interdependent parts, namely, the composition itself and the preparation of an immediately applicable solution whereby the solid compound polyvinylpyrrolidone may be transformed into a beautiful and highly useful film upon the hair.

It is understood, of course, that I may make certain substitutions in the solvents disclosed by way of example in the foregoing specification and certain changes in the proportions of my composition without departing from the spirit of the invention.

What I claim is:

1. A substantially water-free sprayable liquid hair styling preparation for applying to the surface of the hair for setting [the] *and* lusterizing the same, comprising polyvinylpyrrolidone, alcohol, and a propellant selected from the group consisting of fluorochloromethanes and fluorochloroethanes.

2. A hair styling preparation for spraying under self-generated pressure upon the surface of the hair for setting and lusterizing thereof, composed of a substantially water-free solution of polyvinylpyrrolidone, absolute ethyl alcohol, and dichlorodifluoromethane.

3. A hair styling composition for setting and lusterizing the hair by spray application, composed of polyvinylpyrrolidone and di-ethyl phthalate mutually dissolved as a substantially water-free solution in ethyl alcohol in combination with dichlorodifluoromethane as a propellant.

4. A substantially water-free hair styling preparation suitable for spray application for setting and lusterizing the hair, comprising from 4 to 8 percent of polyvinylpyrrolidone in an ethyl alcohol solution, and a propellant selected from the group consisting of fluorochloromethanes and fluorochloroethanes.

5. As a hair styling preparation, a substantially water-free ethyl alcohol solution of polyvinylpyrrolidone in combination with dichlorodifluoromethane as a propellant, for effecting the spray application of the solution onto hair.

6. A substantially water-free hair styling composition for spray application for setting and lusterizing the hair, comprising a mixture of at least 4 percent polyvinylpyrrolidone dissolved in alcohol, with a propellant selected from the group consisting of fluorochloromethanes and fluorochloroethanes.

7. A substantially water-free hair styling composition for spray application for setting and lusterizing the hair, comprising from 4% to 8% of polyvinylpyrrolidone in solution in absolute ethyl alcohol and, as a propellant, dichlorodifluoromethane.

8. A sprayable hair-preparation, comprising a substantially water-free alcoholic solution of polyvinylpyrrolidone and Freon.

9. A sprayable hair preparation comprising Freon, and a substantially water-free alcoholic solution of a product essentially consisting of polymerized units of the structure

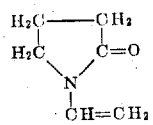

*10. A process of holding and lusterizing human hair for cosmetic effect, comprising applying to the hair a substantially water-free alcoholic solution of polyvinylpyrrolidone.*

*11. A process of holding and lusterizing human hair for cosmetic effect, comprising applying to the hair a substantially water-free alcoholic solution of a product essentially consisting of polymerized units of the structure*

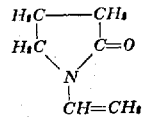

References Cited in the file of this patent or the original patent

UNITED STATES PATENTS

| | | |
|---|---|---|
| 2,070,167 | Iddings | Feb. 9, 1937 |
| 2,143,641 | Bennett | Jan. 10, 1939 |
| 2,305,356 | Luckenbach | Dec. 15, 1942 |
| 2,372,982 | Richards | Apr. 3, 1945 |
| 2,658,045 | Schidknecht | Nov. 3, 1953 |

FOREIGN PATENTS

| | | |
|---|---|---|
| 84,595 | Argentina | May 22, 1947 |
| 902,282 | France | Aug. 23, 1945 |
| 716,197 | Germany | Mar. 12, 1942 |

OTHER REFERENCES

Goodhue: "Low and Moderate Pressure Liquefied-Gas Aerosols," Ind. and Eng. Chem., July 1949, pp. 1523–1527.

Plasdone: G.A.F., New Product Bull., No. P–100, June 15, 1951, 22 pages.

Janistyn: "Reichstoffe, Seifen, Kosmetika," Hutig, Heidelberg, 1950, vol. I, pp. 256, 328 and 329, vol. II, pp. 159–164.

"PVP," Gen. Aniline and Film Corp., N.Y.C., March 1951, pp. 111–113, 141, 142 and 146.

Cooper: "Compressed Gas Aerosols Expand Their Uses," Chem. Ind., December 1948, pp. 970, 972, and 1058.

Fulton: "Propellants for Low-Pressure Liquefied Gas Aerosols," Ind. and Eng. Chem., April 1948, pp. 699 and 700.

Lesser: "Pressure Propelled Products," D. and C. Ind., October 1949, pp. 396–398, 470–473.

Murat: "Etude de certaines propriété chimiques et pharmacodynamiques de la polyvinylpyrrolidone," Produits Pharmaceutiques, August 1949, pp. 350–356.